(12) United States Patent
Hidaka et al.

(10) Patent No.: US 8,394,134 B2
(45) Date of Patent: Mar. 12, 2013

(54) HEAT GENERATING DEVICE

(75) Inventors: Yuki Hidaka, Tokyo (JP); Atsushi Suzuki, Tokyo (JP); Ichiro Sakamoto, Tokyo (JP); Keiji Yoshii, Tokyo (JP)

(73) Assignee: Kao Corporation, Tokyo (JP)

( * ) Notice: Subject to any disclaimer, the term of this patent is extended or adjusted under 35 U.S.C. 154(b) by 582 days.

(21) Appl. No.: 12/522,482

(22) PCT Filed: Feb. 8, 2008

(86) PCT No.: PCT/JP2008/052103
§ 371 (c)(1),
(2), (4) Date: Jul. 8, 2009

(87) PCT Pub. No.: WO2008/099770
PCT Pub. Date: Aug. 21, 2008

(65) Prior Publication Data
US 2010/0023099 A1    Jan. 28, 2010

(30) Foreign Application Priority Data

Feb. 16, 2007  (JP) .................................. 2007-35648
Mar. 9, 2007  (JP) .................................. 2007-60850

(51) Int. Cl.
*A61F 7/00*  (2006.01)
(52) U.S. Cl. .................... 607/108; 607/112; 607/114
(58) Field of Classification Search .................. 607/114, 607/96, 108–112
See application file for complete search history.

(56) References Cited

U.S. PATENT DOCUMENTS

| | | | | |
|---|---|---|---|---|
| 5,046,479 A | * | 9/1991 | Usui | .......................... 126/204 |
| 5,178,139 A | * | 1/1993 | Angelillo et al. | ............. 607/114 |
| 5,366,492 A | * | 11/1994 | Ueki | ............................. 607/114 |
| 5,674,270 A | * | 10/1997 | Viltro et al. | .................... 607/112 |
| 6,629,964 B1 | * | 10/2003 | Ono et al. | ..................... 604/304 |
| 2003/0050615 A1 | * | 3/2003 | Sakamoto et al. | ............ 604/358 |

FOREIGN PATENT DOCUMENTS

| | | |
|---|---|---|
| JP | 3 21320 | 3/1991 |
| JP | 3 96816 | 10/1991 |
| JP | 10-155827 | 6/1998 |
| JP | 11-155895 | 6/1999 |
| JP | 11 512954 | 11/1999 |

(Continued)

OTHER PUBLICATIONS

U.S. Appl. No. 12/675,121, filed Feb. 25, 2010, Hidaka, et al.

(Continued)

*Primary Examiner* — Linda Dvorak
*Assistant Examiner* — Adam Avigan
(74) *Attorney, Agent, or Firm* — Oblon, Spivak, McClelland, Maier & Neustadt, L.L.P.

(57) ABSTRACT

A heat generating device includes an air-permeable first side located proximal to a wearer's body, a second side located distal to a wearer's body, and a heat generating member between the two sides. The second side includes an adhesive layer for attaching the device to a garment. The first side is formed of a nonwoven fabric having an uneven surface topography. The nonwoven fabric includes a first fiber layer, inclusive of a first surface of the fabric, and a second fiber layer, inclusive of a second surface of the fabric, partly bonded to each other and including a large number of protrusions and recesses on the side of the first fiber layer. The first surface is used as the first side.

15 Claims, 10 Drawing Sheets

FOREIGN PATENT DOCUMENTS

| | | |
|---|---|---|
| JP | 2001 507593 | 6/2001 |
| JP | 2001-198150 | 7/2001 |
| JP | 2004-8564 | 1/2004 |
| JP | 2006-204733 | 8/2006 |
| JP | 2006-314585 | 11/2006 |
| JP | 2006-333936 | 12/2006 |
| WO | WO 97/49361 A1 | 12/1997 |
| WO | WO 98/29063 | 7/1998 |

OTHER PUBLICATIONS

Extended European Search Report issued Jun. 26, 2012 in European Patent Application No. 08710982.3.

* cited by examiner (a)

(b)

(a)

(b)

HEAT GENERATING DEVICE

TECHNICAL FIELD

The present invention relates to a heat generating device used to warm a body part, particularly a heat generating device used to alleviate menstrual cramps.

BACKGROUND ART

Various heat generating devices of the type having a heat generating material sealed in an air-permeable flat bag which are used to warm a body part by the heat generated by the heat generating material are known. For example, Patent Document 1 assigned to the common assignee of the present invention proposes a portable body warmer including a heat generating main body and a flap. The heat generating main body includes an outside layer, an inside layer, and a heat generating element interposed between the outside and inside layers. The flap extends outward from an upper edge of the heat generating main body and is designed to be attached to panties (undergarment) when the body warmer is used. Both the heat generating main body and the flap have an adhesive applied thereto so that the heat generating main body is attached to the outer side of panties via the adhesive, while the flap is folded over the waist opening of the panties and attached to the inner side of the panties. Therefore, the position where the body warmer is attachable is limited to near the waist opening of the wearer's panties. Since the heat from the body warmer is transmitted to the body indirectly via the panties, the heat transfer efficiency can vary depending on the textile material of the undergarment.

Apart from the portable body warmer described above, a thermal body pad for relieving menstrual pain is proposed in Patent Document 2. The thermal body pad includes a plurality of heat cells having an exothermic material sealed in between two layers and has a first side with oxygen permeability and a second side which is to be placed directly against a user's body. The oxygen permeable first side is provided with a self-adhesive attachment means for releasably fixing the body pad. The attachment means is provided over the whole area of the first side, via which the body pad is attached to an inside portion of a user's undergarment. Since the self-sensitive attachment means is provided on the whole area of the first side, if the body pad is attached to user's panties with its upper portion sticking from the waist opening of the panties, the adhesive attachment means of the sticking portion would adhere to other user's clothing. Even when the body pad is attached to a right position of user's panties, attachment and/or removal of the body pad are liable to cause pubic hair to adhere to the self-adhesive attachment means. The user's fingers are also apt to be caught by the self-adhesive attachment means in attaching and/or removing the body pad. That is, the body pad lacks handling convenience. Although the body pad applied directly to a user's body on its second side achieves direct heat transfer, a number of the heat cells provides a lumpy feel to the body to cause discomfort.

Besides the body pad of Patent Document 2, known heat generating devices having an adhesive attachment means include a heat generating pack having a heat generating composition sealed in a flat pack having an air permeable adhesive side and a non-adhesive side (see Patent Document 3). The heat generating pack is designed to be attached to an inner portion of a user's undergarment on its air-permeable adhesive side so that the air-permeable adhesive side faces opposite to the body thereby maintaining stable air permeation and that the non-adhesive side is brought into contact with a user's body thereby directly warming the body. The adhesive is uniformly and discretely applied to the air-permeable side by printing or coating. Therefore, the heat generating pack has the same disadvantages of the body pad of Patent Document 2. Furthermore, since the air-permeable adhesive side, through which air should pass, faces an undergarment, some undergarment fabrics can interfere with sufficient air supply. Reduction of the area where the adhesive is applied in an attempt to secure air passage can also result in a failure to provide sufficient adhesive strength.

Patent Document 1: JP 11-155895A
Patent Document 2: WO98/29063A1
Patent Document 3: JP 2001-198150A

DISCLOSURE OF THE INVENTION

The present invention provides a heat generating device having a first side that is adapted to be located proximal to a wearer's body and has air permeability, a second side that is adapted to be located distal to a wearer's body, and a heat generating member interposed between the first and second sides. The second side is provided with an adhesive layer for attaching the heat generating device to a garment. The first side is formed of a nonwoven fabric with an uneven surface. The nonwoven fabric has a first surface and a second surface and includes a first fiber layer inclusive of the first surface and a second fiber layer inclusive of the second surface. The first and second fiber layers are partly bonded to each other. The nonwoven fabric has a large number of protrusions and recesses on its first fiber layer side. The first surface of the nonwoven fabric is used as the first side of the heat generating device.

The present invention also provides a heat generating device having a first side that is adapted to be located proximate to a wearer's body and has air permeability, a second side that is adapted to be located distal to a wearer's body, and a heat generating member interposed between the first and second sides. The heat generating device has a horizontal direction X, a vertical direction Y, an upper and a lower edge extending in the horizontal direction X, side edges extending in the vertical direction Y, and a shape elongated in the horizontal direction X. The second side is provided with an adhesive layer for attaching the heat generating device to a garment. The adhesive layer is located in a region except a strip-shaped central region A extending along the centerline $C_L$ extending in the vertical direction Y and reaching the upper and lower edges, an upper strip-shaped region B extending along the upper edge in the horizontal direction X and reaching both side edges, and a lower strip-shaped region C extending from the center of the lower edge to the opposite directions along the lower edge in the horizontal direction X.

The present invention also provides a method of using the above described heat generating device. The method includes attaching the heat generating device to the inner side of the front portion of the panties by holding the heat generating device with the user's thumb put on the first side and the other finger on the strip-shaped central region which faces the user's panties and, upon detachment, detaching the heat generating device from the panties by holding the device between the user's thumb put on the first side and the other finger which is inserted between the device and the panties along the strip-shaped central region.

DETAILED DESCRIPTION OF THE INVENTION

Figure 1:
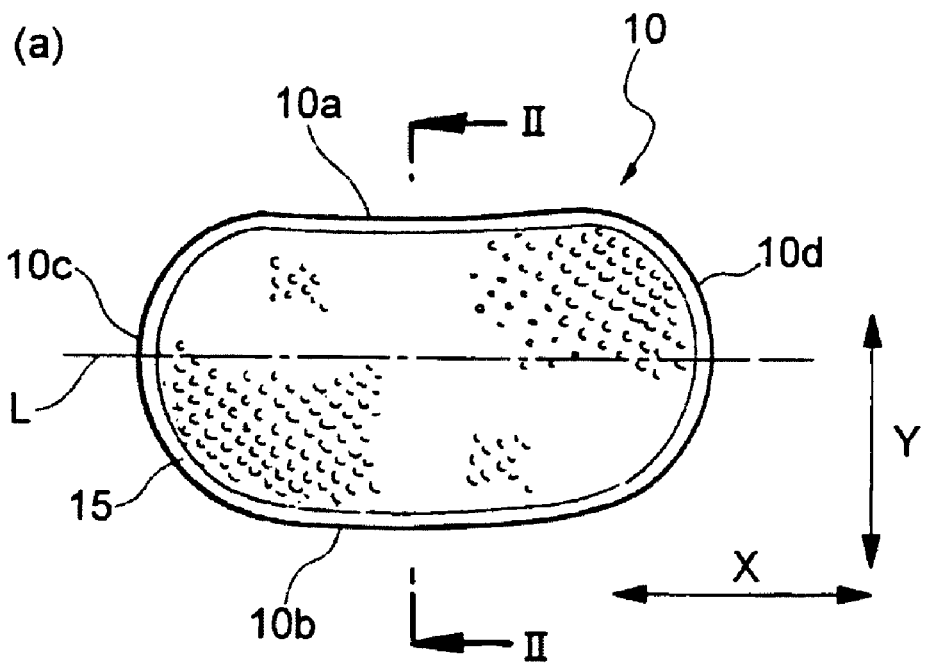
FIG. 1(a) is a plan of a moist heating device as an embodiment of the heat generating device according to the present invention, seen from its skin contacting side.
FIG. 1(b) is a plan of the moist heating device seen from its garment contacting side.
Figure 1:
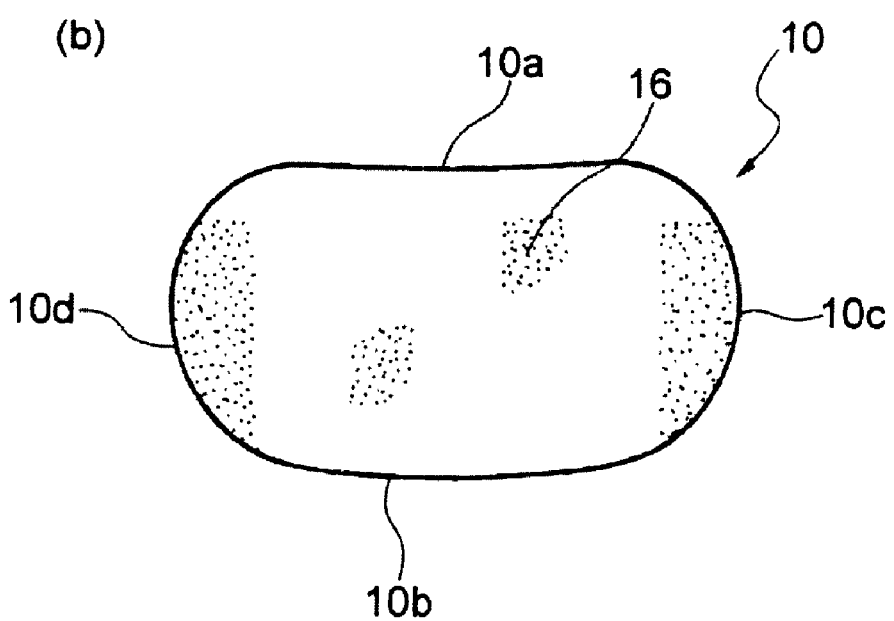

The present invention will be described based on its preferred embodiments with reference to the accompanying drawings. FIG. 1(a) presents a plan of a moist heating device as a first embodiment of the heat generating device according to the present invention, seen from its skin contacting side, and FIG. 1(b) is a plan of the same moist heating device seen from its garment contacting side. FIG. 2 is a cross-sectional view taken along line II-II of FIG. 1(a).

The moist heating device 10 of the first embodiment is designed to generate steam at a prescribed elevated temperature from its heat generating member and apply the steam to a wearer's body to improve wearer's physiological functions. The moist heating device 10 of the present embodiment is especially suited for applying steam heated to a prescribed elevated temperature to the lower abdomen of a female to ease menstrual cramps.

The moist heating device 10 has a horizontal direction X and a vertical direction Y perpendicular to the direction X and has a shape elongated in the horizontal direction X. The moist heating device 10 has an upper edge 10a and a lower edge 10b both extending in the horizontal direction X and opposing side edges 10c and 10d extending in the vertical direction Y. The upper edge 10a has a curved geometry such that the edge is convex inwardly toward the centerline L extending in the horizontal direction X of the moist heating device 10. The lower edge 10b has a curved geometry such that the edge is convex outwardly relative to the centerline L. The side edges 10c and 10d have a curved geometry such that the edges are each convex outwardly. Both ends of the upper edge 10a connect to the upper ends of the respective side edges 10c and 10d, depicting smooth curves. Similarly both ends of the lower edge 10b connect to the lower ends of the respective side edges 10c and 10d, depicting smooth curves. Having a smoothly curved contour as described, the moist heating device 10 gives a wearer little discomfort while worn.

The moist heating device 10 includes a heat generating member 11 and a holder 12 holding the heat generating member 11. The holder 12 is flat-shaped and defines the contour of the moist heating device 10. The holder 12 is composed of a plurality of sheets joined together to provide a closed space in which the heat generating member 11 is placed. The flat holder 12 has a first side 13 located proximate to the wearer's skin and an opposite, second side 14 located distal to the wearer's skin.

The heat generating member 11 contains an oxidizable metal. The heat generating member 11 is a part that generates steam of prescribed elevated temperature by making use of the heat accompanying the oxidation reaction between the oxidizable metal and oxygen. The details of the heat generating member 11 will be described later in more detail.

The first side 13 has air permeability to allow for passage of air and steam. The second side 14 is less permeable to air and steam than the first side 13. In other words, the second side 14 is sparingly air-permeable compared with the first side 13 or air-impermeable. Whether the second side 14 is sparingly air permeable or air impermeable is selected as appropriate for the use of the moist heating device 10.

The moist heating device 10 is used with its first side 13 in direct contact with a wearer's body and the second side 14 in direct contact with wearer's clothing (panties in the particular case of the present embodiment as described below). The moist heating device 10 is configured to apply steam generated by the heat generation of the heat generating member 11 directly to the wearer's skin through the first side 13.

Each of the first side 13 and the second side 14 of the moist heating device 10 is formed of a sheet material. The periphery of the sheet material forming the first side 13 and that forming the second side 14 are bonded to each other so that the holder 12 of the moist heating device 10 has a closed loop-shaped peripheral joint 15. The peripheral joint 15 is continuous. The first side 13 and the second side 14 of the holder 12 are not bonded to each other in the region inside the peripheral joint 15. By this configuration, the holder 12 provides a single closed space in which the heat generating member 11 can be put. As illustrated in FIG. 2, the heat generating member 11 occupies practically the whole area of the space formed by the holder 12. That is, the holder 12 contains one heat generating member 11 such that the heat generating member 11 occupies practically the whole area of the holder 12 except the peripheral joint 15. While in FIG. 2 the heat generating member 11 is merely placed in the closed space in the holder 12, the heat generating member 11 and the holder 12 may be partly fixed to each other by means for fixing, such as an adhesive, in a manner that does not interfere with heat generation.

The moist heating device 10 has a properly controlled air permeance through the first side 13 and the second side 14 so that steam may be released preferentially through the first side 13. Specifically, the moist heating device 10 is designed to have a higher air permeance through the second side than the first side. The term "air permeance" as used herein is a value measured in accordance with JIS P8117, which is defined to be the time required for 100 ml of air to pass through an area of 645 mm² under a constant pressure (unit:

sec/100 ml). A higher air permeance means more time needed for air passage, i.e., lower air permeability. In contrast, a lower air permeance means higher air permeability. Air permeance as defined above and air permeability are in a converse relation. Comparing the air permeability between the first side 13 and the second side 14 in the present embodiment, the first side 13 has higher air permeability than the second side 14. That is, the second side 14 is air impermeable or sparingly air permeable (i.e., air permeable but less air permeable than the first side 13) as previously stated.

The holder 12 has a flat shape having the air permeable first side 13 and the opposite, air impermeable second side 14 and is designed to cause moist heat generation through the air permeable first side 13. Alternatively, the holder 12 has a flat shape having the air permeable first side 13 and the opposite, sparingly air permeable second side 14 and is designed to cause moist heat generation through the air permeable first side 13. In the case where the second side 14 is sparingly air permeable, the air permeance of the first side 13 and that of the second side 14 should be controlled so that air may enter the holder 12 preferentially through the second side 14 while steam may be released preferentially through the first side 13.

In the case where the second side 14 is sparingly air permeable, it is preferred that the air permeance of the second side 14 is 5 or more times, more preferably 10 or more times as much as that of the first side 13 in order to suppress steam release through the second side 14 while securing an air inflow through that side. It is otherwise preferred that the ratio of the air permeance of the first side 13 to that of the second side 14 (first side/second side ratio) is 0.5 or smaller, more preferably 0.2 or smaller. By so controlling the air permeance, release of steam from the second side 14 can be reduced while increasing release of steam from the first side 13. In the case where the second side 14 is air impermeable, on the other hand, air supply into the holder 12 and release of steam are exclusively done through the first side 13.

When the second side 14 is sparingly air permeable, the air permeance of the second side 14 is preferably 30000 sec/100 ml or more, more preferably 40000 sec/100 ml or more, even more preferably 50000 sec/100 ml or more. The air permeance of the first side 13 is preferably 100 to 30000 sec/100 ml, more preferably 1000 to 20000 sec/100 ml, irrespective of whether the second side 14 is air impermeable or sparingly air permeable.

As stated previously, each of the first side 13 and the second side 14 of the moist heating device 10 is formed of a sheet material. Sheet materials that govern air permeance and prevent powder from leaking include melt blown nonwoven fabric and moisture permeable film. Moisture permeable film is obtainable by melt molding a mixture of a thermoplastic resin and an organic or an inorganic filler incompatible with the resin into film and uniaxially or biaxially stretching the film to develop a finely porous structure. Sheet materials having different air permeances and moisture permeances can be combined to make a laminate sheet. Use of such laminate sheets enables further flexible control of air permeances of the first side 13 and the second side 14.

As illustrated in FIG. 2, the first side 13 in the present embodiment is composed of a moisture permeable sheet 13a and a first nonwoven fabric 13b covering the entire area of the sheet 13a. The air permeability of the first side 13 is governed by the air permeability of the moisture permeable sheet 13a because the air permeability of the first nonwoven fabric 13b is sufficiently higher than that of the moisture permeable sheet 13a. The second side 14 is formed of a sheet 14a and a second nonwoven fabric 14b covering the entire area of the sheet 14a. The sheet 14a is moisture permeable or moisture impermeable. When the sheet 14a is moisture permeable, the air permeability of the moisture permeable sheet 14a is less than that of the moisture permeable sheet 13a of the first side 13.

The moisture permeable sheet 13a and the first nonwoven fabric 13b, which constitute the first side 13, are joined together either only at the peripheral joint 15 or all over. When joined all over, the two sheets are bonded discretely so as not to impair air permeability of the moisture permeable sheet 13a. The same applies to the manner of joining the sheet 14a and the second nonwoven fabric 14b, which constitute the second side 14. While the side 13b and the second side 14 of the holder 12 illustrated in FIG. 2 are each composed of two sheets, they may be a laminate of three or more sheets as long as the laminate performs the above described air permeating function. Anyway, the first side 13 that is to be brought into direct contact with the skin is preferably formed of a sheet having the following structure.

As understood from the foregoing description, the holder 12 of the moist heating device 10 of the present embodiment has its exterior surface formed of the first nonwoven fabric 13b and the second nonwoven fabric 14b. The moist heating device 10 feels good to the touch because of its skin contacting side formed of the first nonwoven fabric 13b. Therefore, when applied directly to the skin of a wearer, the moist heating device 10 provides comfort to the wearer. In the present embodiment, in particular, the moist heating device 10 provides not only a better comfort to the wearer but various advantageous effects because of the use of nonwoven fabric described below as the first nonwoven fabric 13b constituting the first side 13, the side to be brought into direct contact with the wearer's skin.

Figure 3:
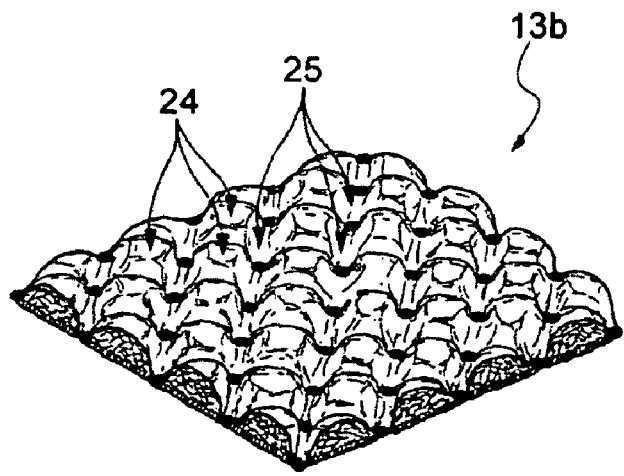
FIG. 3(a) is a fragmentary enlarged view of the nonwoven fabric used in the moist heating device shown in FIG. 1.
FIG. 3(b) is a fragmentary enlarged cross-sectional view of the nonwoven fabric.
Figure 3:
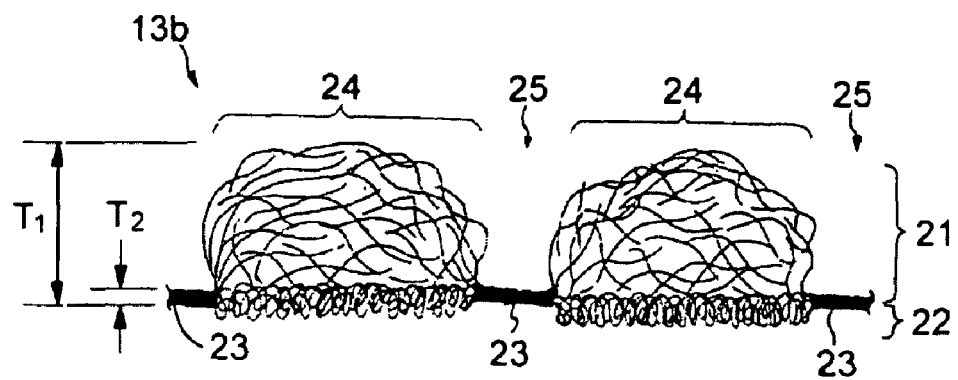

FIG. 3 illustrates a fragmentary enlarged view of the first nonwoven fabric 13b that is well suited for use in the moist heating device 10 of the first embodiment. The first nonwoven fabric 13b has a dual layer structure having a first fiber layer 21 inclusive of one of the surfaces (designated a first surface) and a second fiber layer 22 inclusive of the other surface (designated a second surface). The first fiber layer 21 and the second fiber layer 22 are formed of respective fiber aggregates superposed on each other and joined partly at joints 23. The joints 23 between the first fiber layer 21 and the second fiber layer 22 are formed by compression and densification by heat and/or pressure application so that they are thinner and denser than the other parts of the first nonwoven fabric 13b as illustrated. As a result, the first nonwoven fabric 13b has a large number of protrusions 24 discretely arranged on the side of the first fiber layer 21 in a prescribed pattern and a large number of recesses 25 formed on the joints 23. The first fiber layer 21 of the first nonwoven fabric 13b therefore has an uneven surface topography formed of the protrusions 24 and the recesses 25. The shape of the individual protrusions and recesses is not limited to dots of substantially uniform size as illustrated in FIG. 3(a) and may be a combination of a plurality of shapes such as elongated circles of different size or ridges as long as a comfort to the wearer is secured. The protrusions and recesses may be arranged in a random pattern. The protrusions 24 are filled with fibers. The side of the first fiber layer 21 is used as the first side 13, i.e., the skin-contacting side of the moist heating device 10. Unlike the surface of the first fiber layer 21, the second fiber layer 22 has a generally flat surface topography.

While the moist heating device 10 is in use, the first fiber layer 21, which has the uneven surface topography, is in contact with the wearer's skin mostly on its protrusions 24. That is, the first fiber layer 21 comes into contact with the wearer's skin not all over the area but in parts by a point contact on the protrusions 24. The protrusions 24 are made of fibers to provide good cushioning and high bulkiness, whereby the point contact on the protrusions 24 gives comfort to the wearer. In contrast, the thermal body pad of Patent Document 1 has a lumpy feel due to the heat cells containing an exothermic material such as iron powder and does not give comfort to the wearer as with the moist heating device 10 of the present embodiment.

The moist heating device 10 of the present embodiment has a reduced contact area with the wearer's skin owing to the uneven surface topography of the first fiber layer 21, which prevents skin overhydration during wear. The steam at a prescribed elevated temperature generated by the moist heating device 10 can efficiently be applied to the wearer's skin because the protrusions 24 serve as a spacer between the device 10 and the skin. Moreover, the protrusions 24 as a spacer provide a space for permitting air to flow between the device 10 and the skin. As a result, air is let in smoothly from the first side 13, which is brought into direct contact with the skin, assuring stable continuation of heat and steam generation.

Taking the above effects into consideration, it is preferred that the protrusions 24 of the first nonwoven fabric 13b have a thickness T1 (see FIG. 3(b)) of 1 to 30 mm, more preferably 1 to 10 mm; the recesses 25 have a thickness T2 (see FIG. 3(b)) of 0.01 to 5 mm, more preferably 0.1 to 1 mm; and T1/T2 is 2 to 50, more preferably 2 to 20. It is also preferred for the same considerations that the ratio of the total area of the joints 23 to the area of the first nonwoven fabric 13b (area ratio of the joints 23 per unit area of the first nonwoven fabric 13b) is 3% to 50%, more preferably 5% to 35%; the area of the individual joints 23 is 0.1 to 5 $mm^2$, more preferably 0.1 to 1 $mm^2$; and the smallest distance between adjacent protrusions 24 (the distance between the center of a protrusion and the center of an adjacent protrusion) is 0.5 to 15 mm, more preferably 1 to 10 mm.

The thickness T2 of the recesses 25 and the substantial thickness T1 of the protrusions 24 are measured on a photograph or an image of a cross-section of the first nonwoven fabric 13b with no pressure applied. In the present invention, the first nonwoven fabric 13b is cut along a line passing the crest of a protrusion 24 and a recess 25, and the cut area profile is observed under a microscope VH-8000 from Keyence Corp. to measure the thickness T2 of the recess 25 and the substantial thickness T1 of the protrusion 24.

The first nonwoven fabric 13b preferably has a basis weight of 20 to 200 $g/m^2$, more preferably 40 to 150 $g/m^2$. The basis weight is obtained by cutting a piece of 50 mm by 50 mm or greater size out of the first nonwoven fabric 13b, weighing the piece with an electron balance having a minimum readability of 1 mg, and converting the weight to a per unit area basis.

Since both the first fiber layer 21 and the second fiber layer 22 including the first and the second surfaces, respectively, of the first nonwoven fabric 13 are formed of a fiber aggregate as described, the first nonwoven fabric 13b has a sufficiently higher air permeability than the moisture permeable sheet 13a so that the air permeability of the first side 13 is governed by the air permeability of the moisture permeable sheet 13a. To secure sufficient air permeability, the air permeance (JIS P8117) of the first nonwoven fabric 13b is preferably 0.6 sec/100 ml or less, more preferably 0.4 sec/100 ml or less. The lower limit of the air permeance is preferably about 0.3 sec/100 ml.

The first nonwoven fabric 13b allows for air flow in a horizontal direction (a direction perpendicular to the sheet thickness) because of the uneven surface topography of the first fiber layer 21. The air flow can be retained even under a prescribed pressure. Specifically, the first nonwoven fabric 13b preferably has an air transmission rate of 10 to 500 ml/($cm^2$·sec), more preferably 20 to 200 ml/($cm^2$·sec), in the horizontal direction under a pressure of 50 cN/$cm^2$. When the air transmission rate in a horizontal direction (hereinafter "horizontal air transmission rate") under a pressure of 50 cN/$cm^2$ is 10 ml/($cm^2$·sec) or more, a horizontal air transmission can be maintained sufficiently, and a space is secured between the fabric 13b and the skin through which air is allowed to flow in, even when the first nonwoven fabric 13b is strongly pressed while the moist heating device 10 is worn and brought into intimate contact with the wearer's body. The first nonwoven fabric 13b is therefore no hindrance to the reaction of the heat generating member 11 as compared with common nonwoven fabrics. To put it another way, even if the first nonwoven fabric 13b is pressed and brought into intimate contact with the wearer's body while the moist heating device 10 is worn, a sufficient air flow in the horizontal direction (the direction perpendicular to the sheet thickness) can thus be secured, whereby air continues to be supplied to the heat generating member 11, and heat generation continues in a stable manner. Accordingly, satisfactory heat generation can be achieved without relying on the air permeability of the second side 14. This means that the area of the second side 14 to which an adhesive is applied can be designed freely without taking care not to interfere with air passage. Additionally, skin overhydration during wear of the moist heating device 10 is prevented effectively, providing assured prevention of discomfort or skin problems such as itches and rash due to overhydration.

Figure 6:
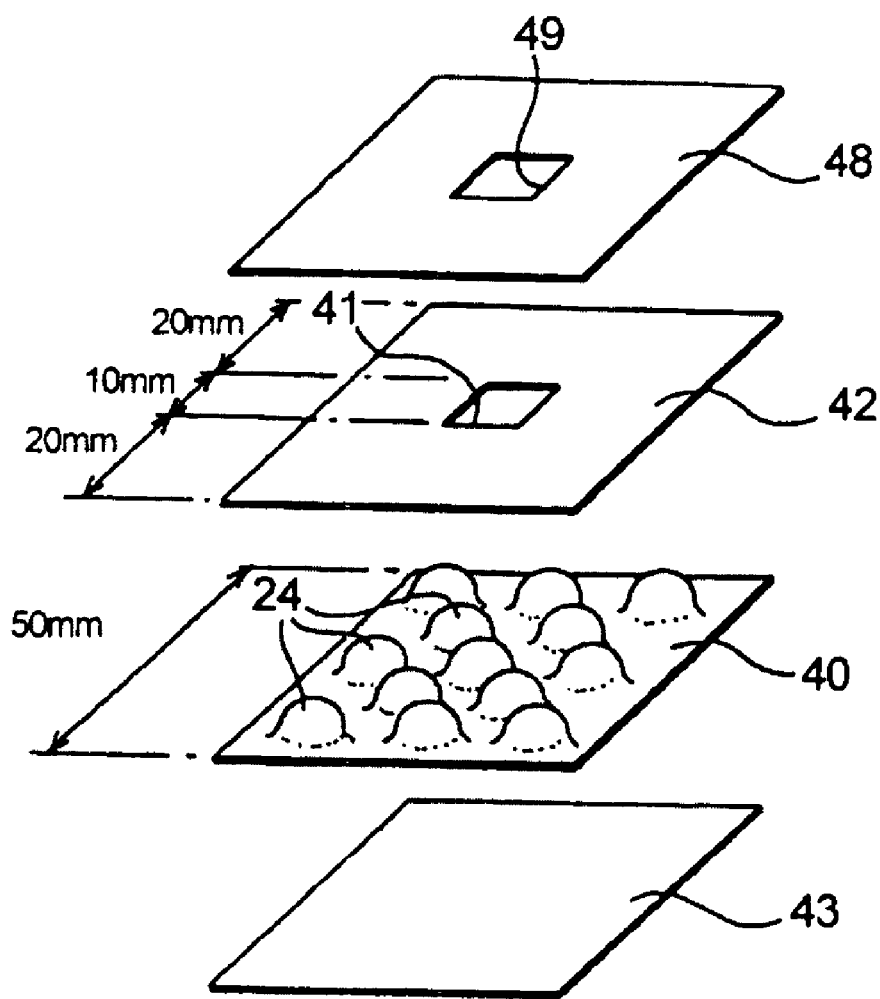
FIG. 6 illustrates a device used to measure a horizontal air transmission rate of a first nonwoven fabric.
Figure 7:
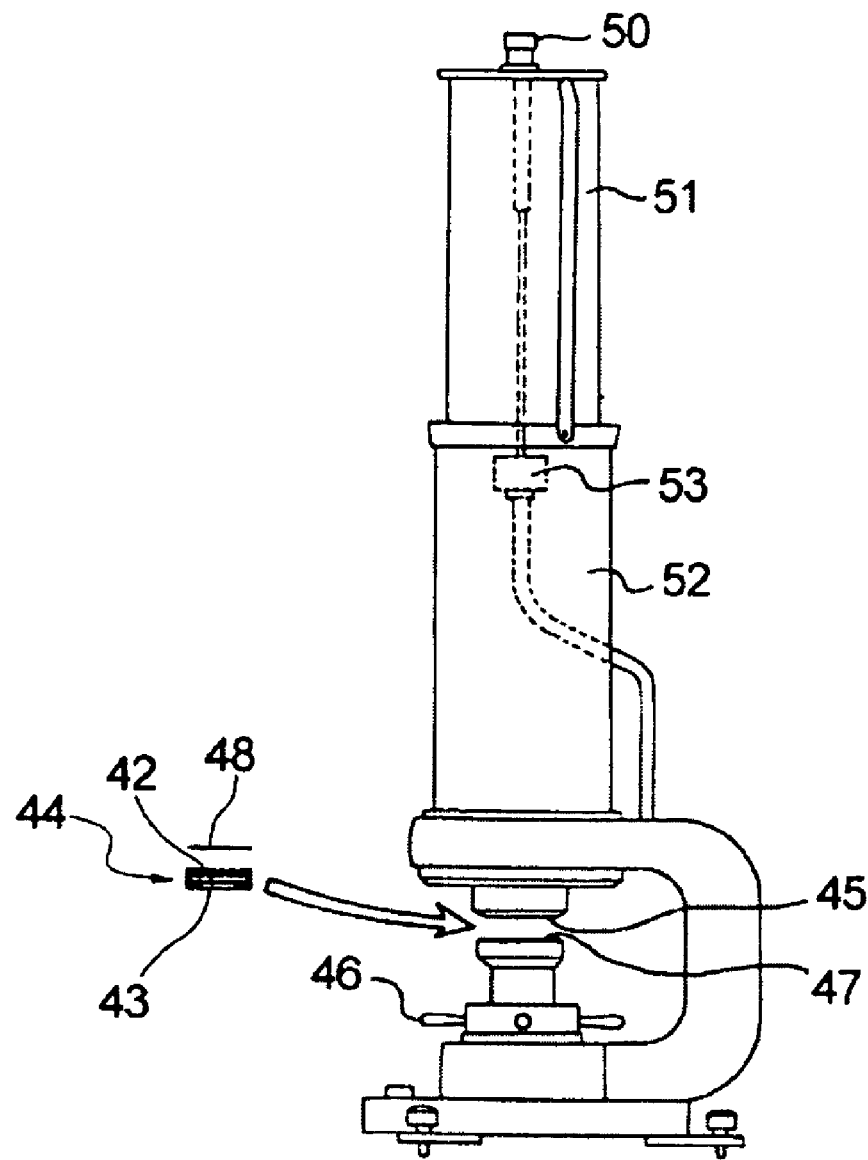
FIG. 7 illustrates an apparatus used to measure a horizontal air transmission rate of a first nonwoven fabric.

The horizontal air transmission rate under a pressure of 50 cN/$cm^2$ is measured as follows. First of all, the thickness T3 of a first nonwoven fabric 13b under a pressure of 50 cN/$cm^2$ is measured. As illustrated in FIG. 6, a 50 mm-side square is then cut out of the first nonwoven fabric 13b to provide a specimen 40. The specimen 40 is sandwiched between a first acrylic resin plate 42 of a size 50 mm×50 mm×3 mm and having a 10 mm-side square opening 41 in the central portion thereof and a second acrylic resin plate 43 of the same size as the first acrylic resin plate 42 but having no opening, with the side of the specimen 40 that is to face a wearer (the side with the protrusions 24) facing the first acrylic plate 42, to prepare a laminate 44 for measurement (see FIG. 7). As illustrated in FIG. 7, the laminate 44 is set in a Gurley tester (type B) specified in JIS P8117, under the gasket 45, with the side of the first acrylic resin plate 42 up. The specimen 40 is compressed to the thickness T3. Air is introduced into the central part of the specimen 40 kept at the thickness T3 through the opening 41, and the time required for introducing 300 ml of air is measured. The amount (ml) of air introduced per unit area (1 $cm^2$ of the opening 41)×1 second is calculated as a horizontal air transmission rate under a load of 50 cN/$cm^2$.

The thickness T3 is measured with a KES compression tester (e.g., KES-FB3, included in "KES-FB" Series, from Kato Tech Co., Ltd.). A KES compression tester has an indenter and a receiver, between which a specimen is sandwiched and compression deformed in the thickness direction at a constant rate. A specimen with a greater size than the indenter is cut out of the first nonwoven fabric 13b and set on the receiver. The indenter is moved down at a speed of 1.2 mm/min to compress the specimen 40 between the indenter and the receiver. When the compression load reaches 50 cN/$cm^2$, the distance between the indenter and the receiver, which corresponds to the thickness of the specimen 40, is measured to give the thickness T3 of the first nonwoven fabric 13b under a load of 50 cN/$cm^2$.

A Gurley tester (B type) that can be used to measure the horizontal air transmission rate is exemplified by Gurley Densometer supplied by Kumagai Riki Kogyo K.K., which is shown in FIG. 7. Compression of the laminate 44 and air-introduction under the compression with the equipment shown in FIG. 7 are carried out as follows. The laminate 44 is positioned under a gasket 45 with the first acrylic plate 42 up, and a clamping handle 46 is turned to adjust the clearance between the gasket 45 and the opposing side 47 so that the specimen 40 may have the intended thickness under load (thickness T3). Numeral 48 in FIGS. 6 and 7 is a silicone plate (hardness: 50) having a 10 mm-side square opening 49 in the central portion thereof, which is inserted between the gasket 45 and the first acrylic plate 42 so that air introduced may not leak through any gap other than the cut edges of the specimen 40. An inner cylinder 51 is lifted by its knob 50 to cause outer air to be sucked into an outer cylinder 52 and then let down into the outer cylinder 52. Thus, 300 ml of air is introduced from an air feed opening (not shown) at the center of the lower side of the gasket 45 into the central portion of the upper side of the specimen 40. The pressure of air introduction depends on the mass of the inner cylinder. The time required for 300 ml of air to be introduced is measured, and the horizontal air transmission rate under 50 cN/cm$^2$ load is calculated. Numeral 53 in FIG. 7 is a photosensor having a combination of a projector and a receptor. A strip with a slit at a predetermined position which is attached to the inner cylinder passes between the projector and the receptor downward to provide signals to a digital counter, whereby the above-defined time is digitally displayed.

The fibers constituting each fiber layer composing the first nonwoven fabric 13b will be described. The second fiber layer 22 contains three-dimensionally crimped fibers. Three-dimensionally crimped fibers usually have a helical crimp. The three-dimensionally crimped fibers are preferably self-crimping fibers having developed a crimp. The second fiber layer 22 may be made solely of the three-dimensionally crimped fibers or may contain other fibers. The other fibers include general thermoplastic resin fibers, regenerated fibers such as rayon, and natural fibers such as cotton. In the case where the second fiber layer 22 contains other fibers in addition to the three-dimensionally crimped fibers, the proportion of the other fibers is preferably 1% to 50% by weight, more preferably 5% to 30% by weight, based on the total weight of the second fiber layer 22. Examples of the fibers constituting the first fiber layer 21 include general thermoplastic resin fibers, regenerated fibers such as rayon, and natural fibers such as cotton. The first fiber layer 21 may contain three-dimensionally crimped fibers. It is preferred that the first fiber layer 21 is made of, or contain, thermoplastic polymer fibers that have substantially no heat shrinkability or do not shrink at or below the heat shrinking temperature of the above-mentioned self-crimping fibers.

The first nonwoven fabric 13b is preferably produced as follows. Fiber aggregates that provide the first fiber layer 21 and the second fiber layer 22, respectively, are prepared. The fiber aggregate may be a web of fibers or a nonwoven fabric. Examples of the nonwoven fabric include air-through non-wovens, heat rolled (heat embossed) nonwovens, air-laid nonwovens, and melt-blown nonwovens. The web of fibers is prepared by, for example, carding. It is more preferred to use a nonwoven fabric or a web of fibers as a fiber aggregate providing the first fiber layer 21 and to use a web of fibers as a fiber aggregate providing the second fiber layer 22.

The web providing the second fiber layer 22 preferably contains self-crimping fibers. Before subjected to heat, the self-crimping fibers can be handled in the same manner as usual fibers for nonwovens and, on being heated at a prescribed temperature, develop a three-dimensional helical crimp and shrink. Self-crimping fibers are exemplified by conjugate fibers having an eccentric sheath/core configuration or a side-by-side configuration having two thermoplastic polymer components having different shrinkage percentages. Examples of the self-crimping fibers that develop a three-dimensional crimp on heating include CPP (trade name) from Daiwabo Co., Ltd.

A fiber aggregate providing the first fiber layer 21 is superposed on the fiber aggregate providing the second fiber layer 22, and the two plies are partly joined in a prescribed pattern. Various methods can be used to join the two plies as long as joints 23 are formed in which at least the first fiber layer 21 is thinner than the other portions. For example, heat embossing or ultrasonic embossing is used preferably. The joints 23 may be discrete dots or straight or curved (e.g., wavy) lines, grids, and zig-zags or the like. The individual joints 23 which are discrete dots may be circular, triangular, rectangular or any other shape. The dot-shaped joints 23 can be arranged, for example, in a staggered pattern as shown in FIG. 3(a).

The first fiber layer 21 and the second fiber layer 22 joined together are heated to cause the self-crimping fibers present in the second fiber layer 22 to develop a helical crimp. The heating temperature should be at or above the temperature at which the self-crimping fibers present in the second fiber layer 22 starts thermal shrinkage. Heating is achieved by, for example, blowing hot air in a through-air system. As a result of crimping, the fibers of the second fiber layer 22 located between the joints 23 shrink, whereby the second fiber layer 22 shrinks in its planar directions. On the other hand, the fibers of the first fiber layer 21 do not shrink. It follows that the fibers of the first fiber layer 21 located between the joints 23 have nowhere to move but in the thickness direction to rise to form a large number of protrusions 24 on the side of the first fiber layer 21 between the raised joints 23 while leaving recesses 25 between the protrusions 24, i.e., at the positions corresponding to the joints 23. Thus, the first nonwoven fabric 13b having an uneven surface topography on the side of the first fiber layer 21 is obtained.

While the first side 13 of the moist heating device 10 is defined by the first nonwoven fabric 13 having the above described structure, the second nonwoven fabric 14b defining the second side 14 is not particularly restricted. Commonly used nonwoven fabrics such as air-through nonwovens, spun-bonded nonwovens, hydroentangled nonwovens, chemical bonded nonwovens, and heat bonded nonwovens can be used as the second nonwoven fabric 14b.

While the first nonwoven fabric 13b preferably has the above-specified structure, other nonwoven fabrics such as air-through nonwovens, spun-bonded nonwovens, hydroentangled nonwovens, chemical bonded nonwovens, and heat bonded nonwovens are also usable as the first nonwoven fabric 13b.

The second nonwoven fabric 14b defining the second side 14 has on its surface an adhesive layer 16 (see FIG. 1(b)) for attaching the heat generating device 10 to a wearer's garment, e.g., panties. The adhesive layer 16 is formed by coating or printing the surface of the second nonwoven fabric 14b with an adhesive such as a thermoplastic resin, e.g., an acrylic resin, a vinyl acetate resin or an olefin resin. These resins are preferably non-residue type resins. The adhesive layer 16 may be provided over the whole area, or in part, of the second nonwoven fabric 14b.

Figure 4:
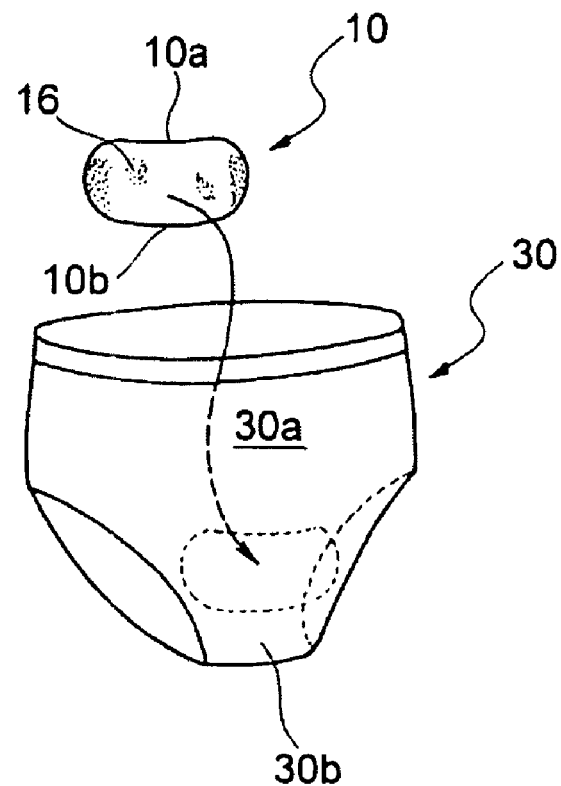
FIG. 4 illustrates the moist heating device of FIG. 1 being about to be attached to panties.

When used, the moist heating device 10 is fixed to the inner side of panties 30 by the adhesive layer 16 with the upper edge 10a located vertically above the lower edge 10b as illustrated in FIG. 4. In this mode of attachment, the horizontal direction X of the moist heating device 10 coincides with the horizontal direction. Since the moist heating device 10 can be attached directly to the inner side of the panties 30, a wearer is able to attach the moist heating device 10 to a desired position of her panties irrespective of the design (low-rise or high-rise) of the panties. When, as illustrated, the moist heating device 10 is attached to a position close to the crotch portion 30b in the front portion 30a of the panties 30, i.e., a position facing the lowest abdomen of a wearer, the device 10 will bring a particularly pronounced effect of easing menstrual pain through steam application to the body. In general, women's panties 30 are high-cut toward the crotch portion 30b in the front portion 30a. The moist heating device 10 the contour of which accommodates the high-cut design would be fixed to a position of the panties corresponding to the wearer's lowest abdomen with good fit. Taking this into consideration, the moist heating device 10 has its lower edge 10b curved outwardly convex relative to the centerline L (see FIG. 1(a)) extending in the horizontal direction X of the most heating device 10.

Figure 5:
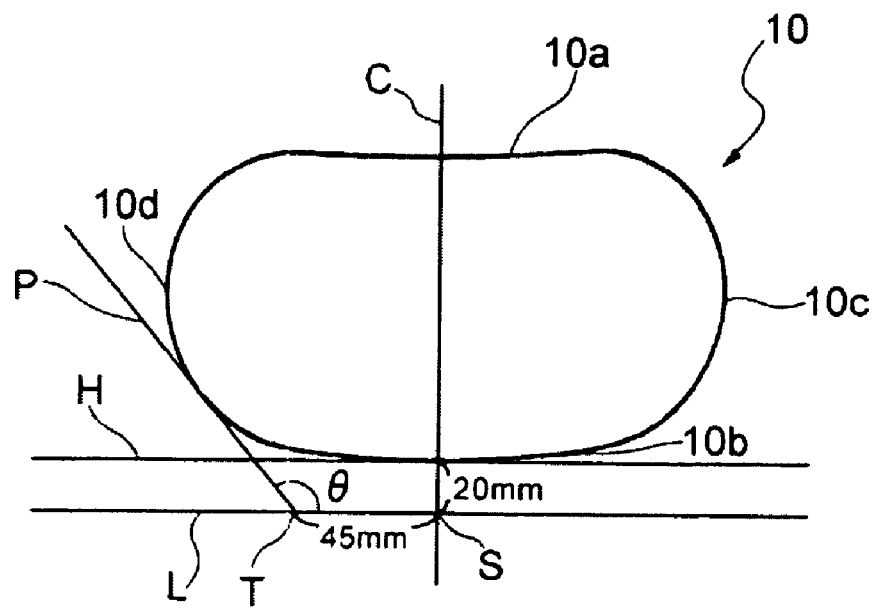
FIG. 5 illustrates how to measure the angle between the lower edge of the moist heating device shown in FIG. 1 and a horizontal line.

To attach the moist heating device 10 to a position corresponding to the wearer's lowest abdomen with better fit, it is preferred for the lower edge 10b and the side edges 10c and 10d to have the following curved geometries. FIG. 5 is referred to. Tangent H is drawn at the lowest point of the lower edge 10b. A straight line L is drawn in parallel to, and 20 mm below, tangent H. Straight line L intersects the vertical centerline C of the moist heating device 10 at point S. A position on straight line L 45 mm apart from point S is taken as point T. Tangent line P of the side edge 10d (or 10c) is drawn to intersect straight line L at point T. The lower edge 10b and the side edges 10c and 10d are preferably curves making an angle θ of 100° to 150°, more preferably 100° to 130°, between tangent P and straight line L. In this connection, it is preferred that the moist heating device 10 measures 120 to 180 mm, more preferably 130 to 160 mm, in direction X (see FIG. 1) and 70 to 100 mm, more preferably 80 to 90 mm, in direction Y (see FIG. 1).

By wearing the moist heating device 10 of the present embodiment in the fashion illustrated in FIG. 4, the heat of steam at a prescribed elevated temperature is applied directly to the wearer's body to effectively alleviate menstrual cramps. This is because heat accompanied by steam generation (i.e., moist heat) is transmitted at a higher rate so that it is more capable of increasing the deep body temperature than heat not accompanied by steam generation (i.e., dry heat). It is considered that a rise in temperature deep in the body stimulates the heat center via the autonomic nerves. It follows that blood vessels dilate, the blood flow increases and the peripheral temperature rises, whereby menstrual pain is eased. Menstrual cramps or pains (primary dysmenorrhea) are known to be caused by prostaglandin (PG)-induced uterine excessive contractions. It is believed that the blood flow increased by heating with the moist heating device 10 prevents PG from retaining in the uterus thereby to ease the pain.

The heat generating member 11 of the moist heating device 10 will be described. The heat generating member 11 contains an oxidizable metal, a reaction accelerator, an electrolyte, and water. The heat generating member 11 has the form of heat generating sheet or powder. In the case when the heat generating member 11 is a heat generating sheet, it is preferably a water-containing fibrous sheet containing an oxidizable metal, a reaction accelerator, a fibrous material, an electrolyte, and water. The heat generating sheet is more preferably a molded sheet containing an oxidizable metal, a reaction accelerator, and a fibrous material and having incorporated therein an aqueous electrolyte solution. The heat generating sheet is exemplified by a sheet shaped by a wet papermaking technique and a laminate structure in which heat generating powder is held in between sheets of paper, etc. Such a heat generating sheet is produced by, for example, the wet papermaking process taught in commonly assigned U.S. Patent Application 2005/0000827A1, the disclosure of which is incorporated herein by reference, or extrusion using a die coater. In the case when the heat generating member 11 is heat generating powder, it is preferably composed of an oxidizable metal, a reaction accelerator, a moisture retaining agent, an electrolyte, and water. A heat generating sheet is preferred to a heat generating powder in terms of uniform application of steam whatever posture a wearer takes. Furthermore, a heat generating sheet is advantageous for a heat generating powder in terms of ease of smoothing out the exothermic temperature distribution and high ability to hold an oxidizable metal.

The heat generating member 11 which is a heat generating sheet is preferably a molded sheet made out of 60% to 90%, more preferably 70% to 85%, of an oxidizable metal, 5% to 25%, more preferably 8% to 15%, of a reaction accelerator, and 5% to 35%, more preferably 8% to 20%, of a fibrous material, all by weight, having incorporated therein 30 to 80 parts by weight, more preferably 40 to 70 parts by weight, per 100 parts by weight of the molded sheet, of a 1% to 15%, more preferably 2% to 10%, by weight aqueous solution of an electrolyte. The heat generating member 11 which is a heat generating powder is preferably a mixture of 20% to 50%, more preferably 25% to 40%, of an oxidizable metal, 3% to 25%, more preferably 5% to 20%, of a reaction accelerator, 3% to 25%, more preferably 5% to 20%, of a moisture retaining agent, all by weight, and 20 parts by weight to 70 parts by weight, more preferably 30 parts by weight to 60 parts by weight, per 100 parts by weight of the solid contents including the oxidizable metal, reaction accelerator, and moisture retaining agent, of a 0.3% to 10%, more preferably 0.5% to 5%, by weight aqueous solution of an electrolyte. The materials constituting the heat generating sheet or heat generating powder can be selected from those commonly used in the art. The materials described in JP 2003-102761 supra are useful as well.

The moist heating device 10 of the present embodiment is packaged in a wrapper (not shown) made of an oxygen barrier material so as to protect the heat generating member 11 from coming into contact with air until use. Materials of such an oxygen barrier wrapper preferably include those having an oxygen transmission rate (ASTM D-3985) of 10 $cm^3 \cdot mm/(m^2 \cdot day \cdot MPa)$ or lower, more preferably 2 $cm^3 \cdot mm/(m^2 \cdot day \cdot MPa)$ or lower. Examples of the oxygen barrier wrapper include a film such as an ethylene-vinyl alcohol copolymer and polyacrylonitrile and a laminate of such a film and vacuum deposited ceramic or aluminum or the like.

The package is preferably labeled to indicate that the moist heating device 10 is for menstrual pain relief. Consumers will be informed by this labeling that the moist heating device of the present invention achieves menstrual pain relieving effects that have heretofore not been achieved sufficiently by conventionally known disposable body warmers. Thus, the good value of the improved performance of the present invention will easily be recognized by consumers. The labeling can contain any kind of information means for conveying information about the improved performance to consumers, including signs and graphics as well as letters. The labeling may contain information to the effect that the product of the present invention is superior to other commercial products. In addition to, or in place of, the labeling on the package, instructions containing the contents of the labeling may be put in the package together with the moist heating device 10. The labeling may be printed directly on the moist heating device 10.

Second to fourth preferred embodiments of the present invention will then be described with reference to FIGS. 8 through 11. The description on the first embodiment applies to these embodiments unless otherwise specified. Thus in FIGS. 8 to 11, common members are identified by the same numerals as in FIGS. 1 to 7.

Figure 8:
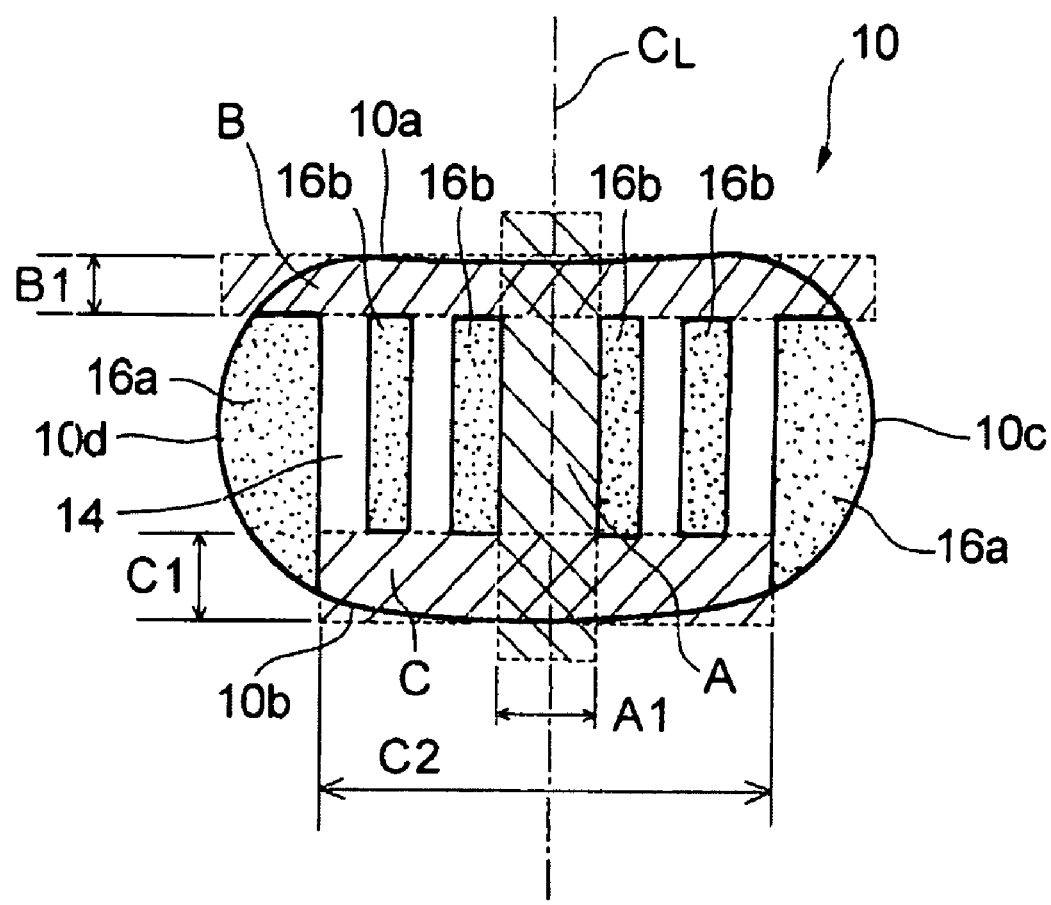
FIG. 8 is a plan of a moist heating device as a second embodiment of the heat generating device according to the present invention, seen from its garment contacting side (corresponding to FIG. 1(b)).
Figure 9:
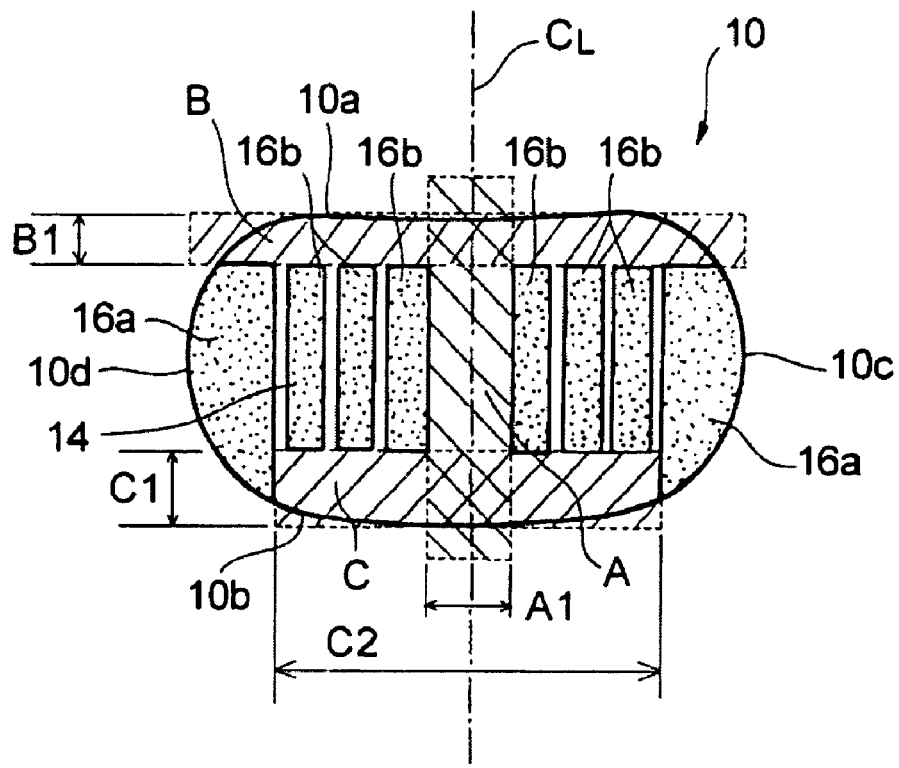
FIG. 9(a) and FIG. 9(b) each show a modification of the moist heating device of FIG. 8 (corresponding to FIG. 1(b)).
Figure 9:
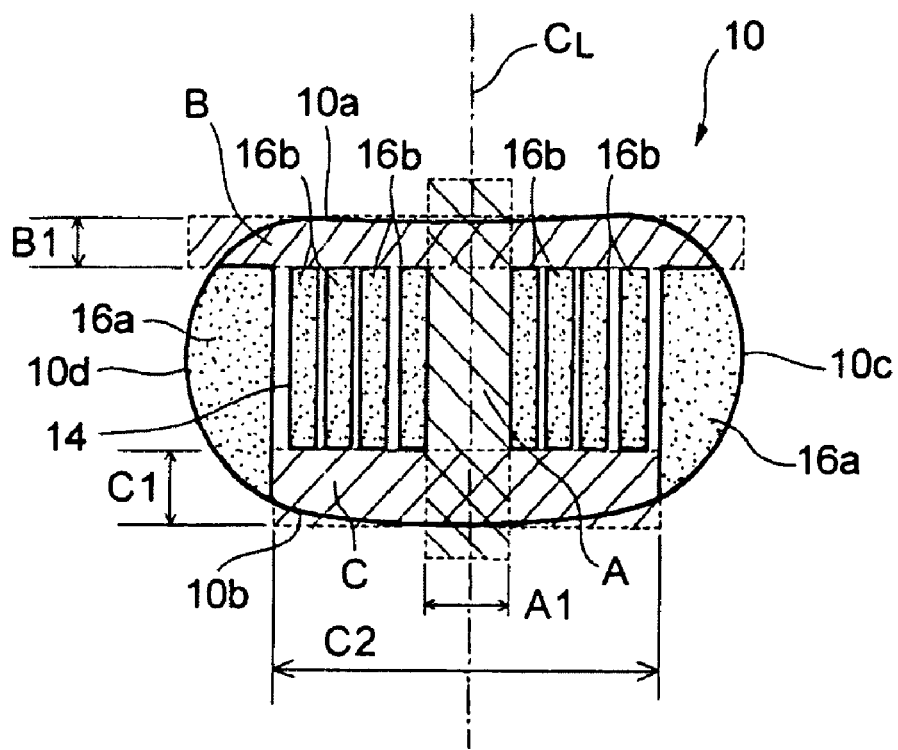

One of the characteristics of the moist heating device 10 of the second embodiment shown in FIG. 8 is the location of adhesive layer including adhesive portions 16a and 16b. The adhesive layer is located in a region except a strip-shaped central region A extending along the centerline $C_L$ extending in the vertical direction Y and reaching the upper and lower edges 10a and 10b, an upper strip-shaped region B extending along the upper edge 10b in the horizontal direction X and reaching both side edges 10c and 10d, and a lower strip-shaped region C extending from the center of the lower edge 10b to both side edges 10c and 10d along the lower edge 10b in the horizontal direction X.

The absence of the adhesive in the central region A prevents the moist heating device 10 from sticking to the wearer's fingers when the wearer attaches and/or detaches the device 10 to and from her panties. This helps smooth attachment and detachment of the device. For example, when in attaching the moist heating device 10 to panties, a user may apply the heat generating device 10 to the inner side of the front portion 30a of her panties 30 smoothly by holding the device 10 with her thumb put on the first side 13 located proximate to the skin and the other finger (e.g., the middle finger) on the strip-shaped central region A on the second side 14 facing the panties 30. For removal, the wearer can easily and smoothly detach the moist heating device 10 from her panties 30 by inserting her finger other than the thumb (e.g., the middle finger) between the device 10 along the strip-shaped central region A and the panties 30 and holding the device 10 between the thumb put on the first side 13 and the other finger.

The absence of the adhesive in the upper strip-shaped region B has the following advantage. Even if a wearer attaches the moist heating device 10 to a wrong position so that the device 10 sticks out of the waist opening of panties 30, the sticking part of the device 10, having no adhesive layer, does not stick to clothing other than the panties. Besides, the presence of the adhesive-free, upper strip-shaped region B helps a wearer to smoothly insert her finger between the panties 30 and the moist heating device 10 and detach the device 10 from the panties 30.

The absence of the adhesive in the lower strip-shaped region C prevents the wearer's pubic hair from adhering to that region. As stated earlier, the moist heating device 10 attached to a position close to the crotch portion 30b in the front portion 30a of the panties 30 produces a particularly pronounced effect of easing the menstrual cramps by steam application to the wearer's body. However, the moist heating device 10 attached to such a position often catches the pubic hair on its adhesive layer. The absence of the adhesive in the lower strip-shaped region C effectively prevents such an inconvenience.

To enhance the above mentioned effects brought by the absence of the adhesive in the strip-shaped central region A, the upper strip-shaped region B, and the lower strip-shaped region C, it is preferred for these regions to have the following sizes regardless of the size of the moist heating device 10. The strip-shaped central region A preferably has a width A1 of 20 mm or greater, more preferably 20 to 100 mm, even more preferably 20 to 50 mm. The upper strip-shaped region B preferably has a width B1 of 5 to 15 mm, more preferably 5 to 10 mm. The lower strip-shaped region C preferably has a width C1 of 20 mm or greater, more preferably 20 to 70 mm, even more preferably 20 to 50 mm, and a length C2 of 70 mm or greater, more preferably 70 to 200 mm, even more preferably 80 to 150 mm. The lower strip-shaped region C may (as in FIG. 8) or may not have both of its longitudinal ends reaching the respective side edges 10c and 10d. The moist heating device 10 preferably measures 50 to 300 mm, more preferably 100 to 200 mm, in the horizontal direction X and 50 to 120 mm, more preferably 50 to 100 mm, in the vertical direction Y.

While the adhesive-free regions on the second side 14 are arranged as described, the regions where an adhesive is applied, i.e., the adhesive layer has the following geometry. The adhesive layer is roughly divided into first adhesive portions 16a and second adhesive portion 16b. The first adhesive portions 16a are a pair of portions extending vertically along the opposite side edges 10c and 10d from the lower edge of the upper strip-shaped region B to the lower edge 10b. The second adhesive portions 16b are two pairs of strip-shaped portions extending vertically from the lower edge of the upper strip-shaped region B to the upper edge of the lower strip-shaped region C between the strip-shaped central region A and each of the first adhesion portions 16a. Each pair of the second adhesive portions 16b are symmetrical about the centerline $C_L$. All the second adhesive portions 16b may or may not be of the same shape. Otherwise, the second adhesive portions 16b may be three or more pairs of strip-shaped portions as illustrated in FIGS. 9(a) and 9(b). In short, the second adhesive portions 16b may be more than one pair.

As illustrated in FIGS. 8, 9(a), and 9(b), the second adhesive portions 16b, which are symmetrical about the centerline $C_L$, are stripes extending in the vertical direction of the moist heating device 10. The moist heating device 10 attached to the inner side of panties 30 with so configured adhesive layer is less likely to come off when, being in the toilet for example, the wearer pulls up and down her panties and yet easy to detach upon detachment. The width of the individual second adhesive portions 16b is preferably 1 to 20 mm, more preferably 5 to 10 mm, provided that the horizontal and vertical sizes of the moist heating device 10 fall within the ranges described supra.

Figure 10:
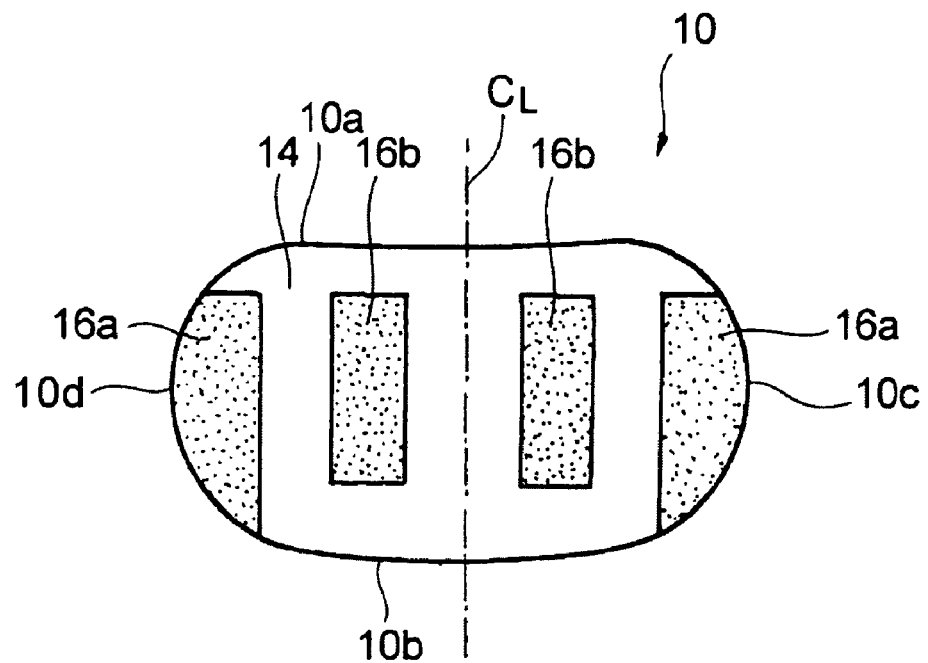
FIG. 10 is a plan of a moist heating device as a third embodiment of the heat generating device according to the present invention, seen from its garment contacting side (corresponding to FIG. 1(b)).

In the third embodiment presented in FIG. 10, the adhesive layer includes a pair of second adhesive portions 16b symmetrical about the centerline CL extending in the vertical direction Y of the moist heating device 10. The individual second adhesive portions 16b are wider than those of the second embodiment. The first adhesive portions 16a are the same as in the second embodiment. According to the third embodiment, the same effects as in the second one are obtained.

Figure 11:
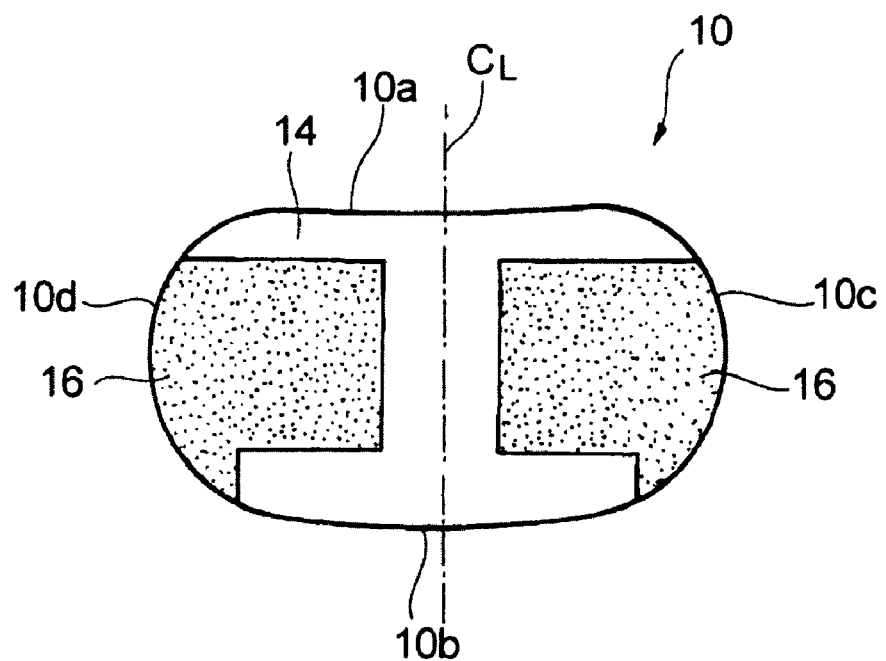
FIG. 11 is a plan of a moist heating device as a fourth embodiment of the heat generating device according to the present invention, seen from its garment contacting side (corresponding to FIG. 1(b)).

In the fourth embodiment illustrated in FIG. 11, the adhesive layer 16 is provided on the entire area except the strip-shaped central region A, upper strip-shaped region B, and lower strip-shaped region C. The adhesive layer 16 is a pair of adhesive portions symmetrical about the centerline $C_L$. According to this embodiment, the moist heating device 10 exhibits increased adhesive strength to the panties 30 and is much less likely to come off when the pair of panties is pulled up and down repeatedly.

While the present invention has been described with reference to its preferred embodiments, the present invention is not limited thereto. For example, while in the second and third embodiments the second adhesive portions 16b are symmetrical with respect to the centerline CL extending in the vertical direction of the moist heating device 10, they do not need to have such symmetry about the centerline CL. The second adhesive portions 16b may be three or more pairs.

While the foregoing embodiments have been described with reference to application to panties as a garment to which the moist heating device 10 is to be attached, the garment to which the moist heating device 10 is to be attached is not limited to panties. The moist heating device 10 may be applied to a variety of clothing depending on the body part needing to be treated by the device.

While the foregoing embodiments relate to application of the heat generating device of the present invention to a moist heating device, the present invention is also applicable to other heat generating devices, including those known as disposable body warmers or heating pads capable of generating heat without being accompanied by substantial steam generation.

EXAMPLES

The present invention will now be illustrated in greater detail with reference to Examples, but it should be understood that the invention is not limited thereto. Unless otherwise noted, all the percents and parts are by weight.

Example 1

(1) Preparation of Heat Generating Member
Preparation of Slurry
(a) Fibrous material: pulp fiber NBKP (Mackenzie (trade name) from Fletcher Challenge Canada, Ltd.; CSF: 140 ml) 8%
(b) Oxidizable metal: iron powder (RKH (trade name) from Dowa Iron Powder Co., Ltd. 83%
(c) Reaction accelerator: activated carbon (Carboraffin (trade name) from Japan EnviroChemicals, Ltd.) 9%

To the mixture of components (a), (b), and (c) above were added 0.7 parts of a polyamide-epichlorohydrin resin (WS4020 from Seiko PMC Corp.) as a cationic flocculant and 0.18 parts of a sodium carboxymethyl cellulose (HE 1500F from Dai-ichi Kogyo Seiyaku Co., Ltd.) as an anionic flocculant per 100 parts of the solid contents of the mixture (the total of compounds (a) to (c)). The mixture was then diluted with industrial water to a solids concentration of 12%.
Papermaking Conditions The slurry thus prepared was diluted with water to 0.3% in front of the head box and drained on an inclined short-wire paper machine at a line speed of 15 m/min to form a wet molded sheet.
Dewatering and Drying Conditions The molded sheet was dewatered between felt blankets, passed as such between 140° C. heated rolls to be dried to a water content of 5% or less. The dried sheet had a basis weight of 450 g/m$^2$ and a thickness of 0.45 mm. As a result of measurement with a thermogravimetric analyzer (TG/DTA 6200 from Seiko Instruments Inc.), the resulting molded sheet was found to be made up of 83% iron, 9% activated carbon, and 8% pulp.
Aqueous Electrolyte Solution
Electrolyte: purified salt (NaCl)
Water: distilled water
Electrolyte concentration: 5%.
Conditions of Electrolyte Addition A stack of three thicknesses of the resulting sheet (4.9×10.8 cm each) was impregnated with a 5% sodium chloride aqueous solution in an amount of 45% of the weight of the molded sheet to prepare a heat generating member of a sheet form.

(2) Preparation of Holder

Figure 2:
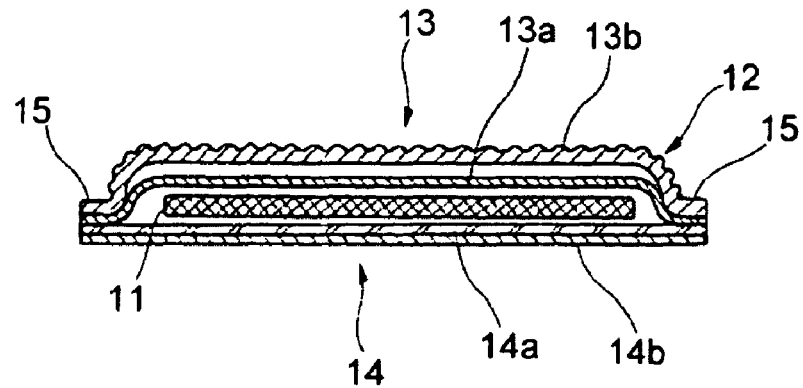
FIG. 2 is a cross-section taken along line II-II in FIG. 1.

A holder having the configuration shown in FIGS. 1 and 2 was made. A porous, moisture permeable polyethylene film (air permeance: 20000 sec/100 ml) was used as a moisture permeable sheet 13a. A nonwoven fabric prepared by the method described below was used as a first nonwoven fabric 13b. The moisture permeable sheet 13a and the nonwoven fabric 13b were joined together only along their perimeters, leaving the inside of the perimeters non-joined. A porous, moisture permeable polyethylene film was used as a sheet 14a. A spun-bonded polyester nonwoven fabric (basis weight: 40 g/m$^2$) was used as a second nonwoven fabric 14b. The sheet 14a and the second nonwoven fabric 14b were joined together with a hot melt adhesive. The resulting laminate of 14a and 14b had an air permeance of 60000 sec/100 ml. The resulting holder was 155 mm in the direction X and 85 mm in the direction Y. The angle θ (see FIG. 5) was 120 degrees.
(3) Preparation of Moist Heating Device The heat generating member was put in the holder to make a moist heating device having the configuration illustrated in FIGS. 1 and 2. The moist heating device was designed to generate heated steam from its first side 13.
(4) Preparation of First Nonwoven Fabric 13b
(a) Preparation of First Fiber Layer 21

Sheath/core conjugate fiber (NBF(H) (trade name, available from Daiwabo Co., Ltd.; 1.1 dtex×51 mm) was carded into a web having a basis weight of 10 g/m$^2$, which was used as a first fiber layer 21. The sheath/core conjugate fiber had polyethylene terephthalate as a core component and polyethylene as a sheath component.
(b) Preparation of Second Fiber Layer 22

Helically self-crimping fiber (CPP (trade name), from Daiwabo Co., Ltd.; 2.2 dtex×51 mm; heat shrink initiation temperature: 90° C.) was carded into a web having a basis weight of 20 g/m$^2$, which was used as a second fiber layer 22.
(c) Preparation of First Nonwoven Fabric 13b The first fiber layer 21 and the second fiber layer 22 were superposed on each other and partly joined together by ultrasonic embossing. The formed joints 23 each had a circular shape with a diameter of 1.5 mm and were arranged in the pattern shown in FIG. 3(a). Hot air at 130° C.±10° C. was blown to the joined layers in a through-air system for about 1 to 10 minutes. As a result, the self-crimping fiber of the second fiber layer 22 developed crimps, and the second fiber layer 22 shrank, whereupon the parts of the first fiber layer 21 between the joints protruded. There was thus obtained a first nonwoven fabric 13b with a great number of protrusions 24 as illustrated in FIGS. 3(a) and 3(b). The inside of the individual protrusions formed of the first fiber layer 21 was filled with fibers as depicted in FIG. 3(b). The resulting first nonwoven fabric 13b had a basis weight of 60 g/m$^2$, in which the basis weight of the first fiber layer 21 was 20 g/m$^2$, and that of the second fiber layer 21 was 40 g/m$^2$. The thickness T1 of the protrusions 24 was 2.0 mm, and the thickness T2 of the recesses 25 was 0.8 mm. The area ratio of the joints 23 was 9%. The horizontal air transmission rate measured by the method illustrated in FIGS. 6 and 7 was 140 ml/(cm$^2$·sec).
(5) Evaluation 1

Figure 12:
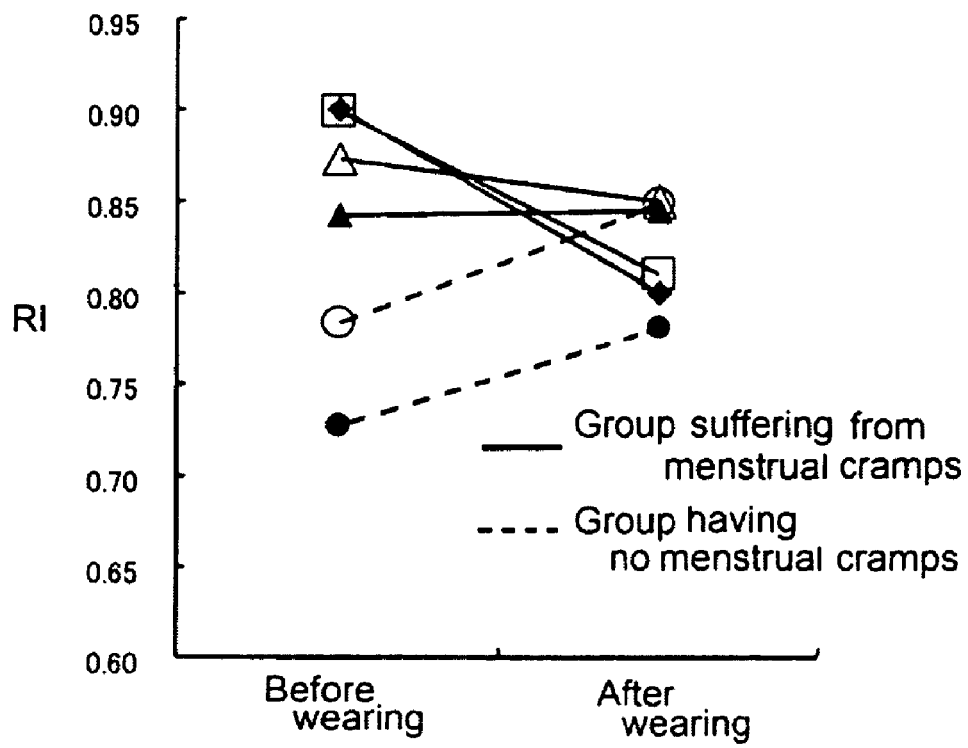
FIG. 12(a) is a graph of RI values of the uterine artery of test subjects measured before and after use of the moist heating device prepared in the Example.
FIG. 12(b) is a graph showing the change of the RI values.
Figure 12:
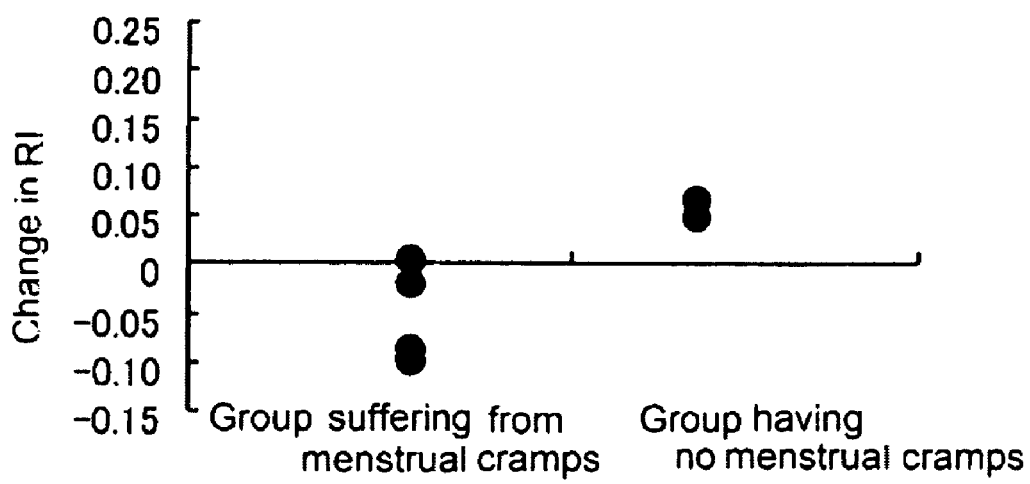

The resulting moist heating device was evaluated for menstrual cramp-alleviating effects as follows. The test subjects were six female students aged on average 21.9±1.5 years. Four out of the six subjects were suffering from menstrual cramps, and the rest were not. The subjects wore the moist heating device on their lower abdomen for 5 hours during their period. The blood flow rate in the subjects' uterine artery was recorded before wearing and after 5-hour wearing using an ultrasonograph (SSD-3500, from Aloka Co., Ltd.) to provide an arterial blood flow pattern, from which maximum systolic blood flow velocity ($V_{max}$) and minimum diastolic blood flow velocity ($V_{min}$) were obtained. Resistance index (RI) was calculated from $V_{max}$ and $V_{min}$, RI being defined to be $(V_{max}-V_{min})/V_{max}$. RI is indicative of peripheral blood vessel resistance. The smaller the RI value, the more smoothly blood flows. The results of RI measurements made before and after wearing the moist heating device are shown in FIG. 12(a). The measurements were taken at 5 to 10 sites per subject to obtain an average RI value. It is seen from the results that four out of six subjects showed a decrease of RI. All the four subjects who showed a decrease of RI were those suffering from menstrual cramps, as is seen from the graph shown in FIG. 12(b). As a result of interviews, all the four subjects suffering from menstrual cramps reported that the menstrual cramp (pain at the lower abdomen) was alleviated. From these results, applying the moist heating device of the invention to the test subjects suffering from menstrual cramps brings about reduction of RI, namely, improved blood flow, whereby the menstrual cramp is eased. While not shown in the drawing, neither a stuffy feeling nor rash caused by the moist heating device worn was reported.

(6) Evaluation 2

Measurement of Skin Surface Temperature

Figure 13:
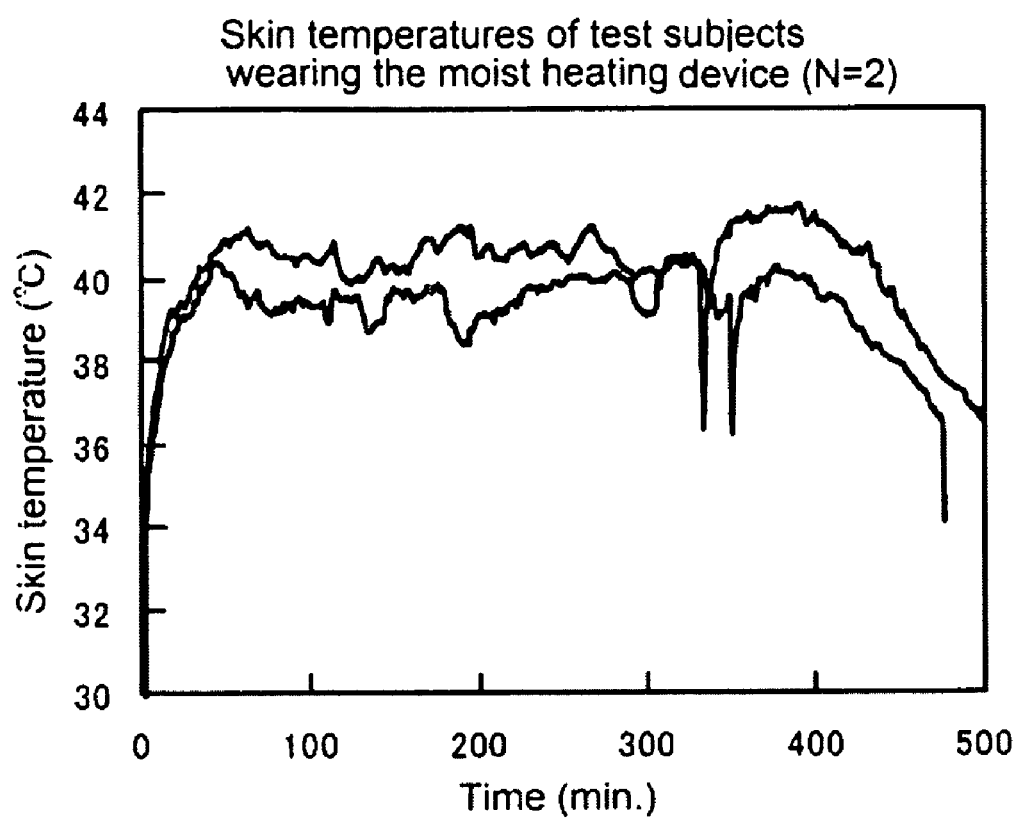
FIG. 13 is a graph of skin temperatures of test subjects wearing the moist heating device prepared in the Example on their skin.

Test subjects wore the resulting moist heating device as attached to the inner side of their panties so that the heat generating member is applied to their lower abdomen, and the temperature of the skin at the center of the application site was monitored using a temperature sensor (handy type temperature data logger LT-8, from Gram Corp.). The results are shown in FIG. 13. It is seen that the skin temperature around 40° C. was maintained for more than 5 hours. The subjects reported no discomfort or stuffy feeling during the monitoring. When the subjects pulled down their panties after 6 to 7 hours from the start of heat generation, the moist heating device did not come off.

INDUSTRIAL APPLICABILITY

As described above, the heat generating device of the present invention, the side of which that comes into direct contact with a wearer's body is formed of nonwoven fabric having an uneven surface topography, is comfortable to wear. The uneven surface topography provides a reduced contact area with the wearer's skin, causing little over-hydration. Furthermore, the uneven topography provides spaces between the wearer's skin and the device through which air can flow so that air is smoothly let in through the side in direct contact with the skin to secure stable continuation of heat generation.

The heat generating device of the present invention is designed not to adhere to wearer's fingers or pubic hair when attached to and detached from the wearer's panties. Even if the heat generating device is attached to stick out of the waist edge of panties by mistake, the heat generating device is designed not to adhere to other clothing.

The invention claimed is:

1. A heat generating device comprising a first side adapted to be located proximate to the skin of a wearer and having air permeability, a second side adapted to be located distal to the skin of the wearer, and a heat generating member located between the first and second sides, wherein
the second side is provided with an adhesive layer for attaching the heat generating device to a garment,
the second side has an air permeance of 30000 to 60000 sec/100 ml,
the first side comprises a nonwoven fabric having an uneven surface,
the nonwoven fabric has a first surface and a second surface and comprises a first fiber layer inclusive of the first surface and a second fiber layer inclusive of the second surface,
the first and second fiber layers are partly bonded to each other,
the nonwoven fabric has a number of protrusions and recesses on its first fiber layer side and a flat surface topography on its second fiber layer side,
the heat generating member includes a heat generating sheet,
the first surface of the nonwoven fabric defines the first side of the heat generating device,
the heat generating device has a horizontal dimension extending in a horizontal direction, a vertical dimension extending in a vertical direction, upper and lower edges extending in the horizontal direction, opposing side edges extending in the vertical direction, and a shape elongated in the horizontal direction, and
the adhesive layer is located in a region except a strip-shaped central region extending along a vertical centerline which extends in the vertical direction and reaches the upper and lower edges, an upper strip-shaped region extending along the upper edge in the horizontal direction, and a lower strip-shaped region extending from a center of the lower edge towards opposing directions along the lower edge in the horizontal direction, such that the upper region forms a flap with none of the adhesive layer located at distal ends of a length of the upper region in the horizontal direction, and the lower region forms a pocket with a portion of the adhesive layer located at distal ends of a length of the lower region in the horizontal direction.

2. The heat generating device according to claim 1, wherein the adhesive layer comprises a pair of first adhesive portions extending in the vertical direction along the opposing side edges from a lower edge of the upper strip-shaped region to the lower edge of the heat generating device, and more than one pair of strip-shaped second adhesive portions extending in the vertical direction from the lower edge of the upper strip-shaped region to an upper edge of the lower strip-shaped region and located between the strip-shaped central region and each of the first adhesion portions.

3. The heat generating device according to claim 1, wherein the lower edge and the side edges have a curved geometry such that, when (1) a first tangent is drawn at the lowest point of the lower edge, (2) a straight line is drawn in parallel to, and 20 mm below, the first tangent, and a position at an intersecting-point of the straight line and the vertical centerline of the heat generating device is taken as a first point, (3) a position on the straight line 45 mm apart from the first point is taken as a second point, and (4) a second tangent of the side edge is drawn to intersect the straight line at the second point, the second tangent and the straight line make an angle between 100° to 150°.

4. The heat generating device according to claim 1, wherein the second side is sparingly air permeable compared with the first side.

5. The heat generating device according to claim 1, wherein the heat generating member is designed to generate steam heated to a prescribed temperature.

6. The heat generating device according to claim 1, wherein the second side has an air permeance of 40000 to 60000 sec/100 ml.

7. The heat generating device according to claim 1, wherein the second side has an air permeance of 50000 to 60000 sec/100 ml.

8. The heat generating device according to claim 1, wherein the first side has an air permeance of 100 to 30000 sec/100 ml.

9. The heat generating device according to claim 1, wherein the first side has an air permeance of 1000 to 20000 sec/100 ml.

10. The heat generating device according to claim 1, wherein the length of the upper region is longer than the length of the lower region.

11. The heat generating device according to claim 1, wherein a width of the upper region, in the vertical direction, is narrower than a width of the lower region, in the vertical direction.

12. The heat generating device according to claim 1, wherein the adhesive layer is provided in areas between the upper and lower regions along the opposing side edges.

13. The heat generating device according to claim 1, wherein the heat generating device is adapted to be located distal to the lower abdomen of the wearer.

14. A heat generating device comprising a first side adapted to be located proximate to the skin of a wearer and having air permeability, a second side adapted to be located distal to the skin of a wearer, and a heat generating member located between the first and second sides and having a horizontal dimension extending in a horizontal direction, a vertical dimension extending in a vertical direction, upper and lower edges extending in the horizontal direction, opposing side edges extending in the vertical direction, and a shape elongated in the horizontal direction, wherein the second side is provided with an adhesive layer for attaching the heat generating device to a garment, the adhesive layer is located in a region except a strip-shaped central region extending along a vertical centerline which extends in the vertical direction and reaches the upper and lower edges, an upper strip-shaped region extending along the upper edge in the horizontal direction, and a lower strip-shaped region extending from a center of the lower edge towards opposing directions along the lower edge in the horizontal direction, such that the upper region forms a flap with none of the adhesive layer located at distal ends of a length of the upper region in the horizontal direction, and the lower region forms a pocket with a portion of the adhesive layer located at distal ends of a length of the lower region in the horizontal direction.

15. A method, comprising:

providing a heat generating device, including a first side adapted to be located proximate to the skin of a wearer and having air permeability, a second side adapted to be located distal to the skin of a wearer, and a heat generating member located between the first and second sides and having a horizontal dimension extending in a horizontal direction, a vertical dimension extending in a vertical direction, upper and lower edges extending in the horizontal direction, opposing side edges extending in the vertical direction, and a shape elongated in the horizontal direction, wherein the second side is provided with an adhesive layer for attaching the heat generating device to a garment, and the adhesive layer is located in a region except a strip-shaped central region extending along a vertical centerline which extends in the vertical direction and reaches the upper and lower edges, an upper strip-shaped region extending along the upper edge in the horizontal direction, and a lower strip-shaped region extending from a center of the lower edge towards opposing directions along the lower edge in the horizontal direction, such that the upper region forms a flap with none of the adhesive layer located at distal ends of a length of the upper region in the horizontal direction, and the lower region forms a pocket with a portion of the adhesive layer located at distal ends of a length of the lower region in the horizontal direction;

attaching the heat generating device to the inner side of the front portion of the panties by holding the heat generating device with the user's thumb put on the first side and the other finger put on the strip-shaped central region which faces user's panties; and, upon detachment, detaching the heat generating device from the panties by holding the device between the user's thumb put on the first side and the other finger which is inserted between the device and the panties along the strip-shaped central region.

* * * * *